(12) United States Patent
Simdon

(10) Patent No.: US 8,357,116 B2
(45) Date of Patent: Jan. 22, 2013

(54) BAG ATTACHMENT DEVICE FOR BREASTPUMP

(75) Inventor: Craig Simdon, Round Lake, IL (US)

(73) Assignee: Medela Holding AG, Baar (CH)

( * ) Notice: Subject to any disclaimer, the term of this patent is extended or adjusted under 35 U.S.C. 154(b) by 0 days.

(21) Appl. No.: 12/853,644

(22) Filed: Aug. 10, 2010

(65) Prior Publication Data

US 2012/0041365 A1    Feb. 16, 2012

(51) Int. Cl.
*A61M 1/06* (2006.01)
(52) U.S. Cl. .......................... 604/74; 604/408
(58) Field of Classification Search .............. 604/74–75, 604/65–66, 891.1, 408; 215/11.1, 11.3–11.5, 215/390, 399; 383/904, 8–10, 22, 26, 34, 383/215; 24/598.4; 222/566–573, 575
See application file for complete search history.

(56) References Cited

U.S. PATENT DOCUMENTS

| | | | |
|---|---|---|---|
| 3,690,524 A * | 9/1972 | Haberhauer | 222/573 |
| 3,757,784 A | 9/1973 | Avery | |
| 3,905,477 A | 9/1975 | Graham | |
| 4,151,929 A * | 5/1979 | Sapien | 220/495.02 |
| 4,420,021 A | 12/1983 | Strand et al. | |
| 4,437,634 A | 3/1984 | Hambleton | |
| 4,558,792 A * | 12/1985 | Cabernoch et al. | 215/11.3 |
| 4,563,864 A | 1/1986 | Eschmann | |
| 4,600,104 A | 7/1986 | Yanase | |
| 4,676,284 A | 6/1987 | DeCrane | |
| 4,798,042 A | 1/1989 | Davis | |
| 4,857,051 A | 8/1989 | Larsson | |
| 5,036,893 A | 8/1991 | DeCrane | |
| 5,109,893 A | 5/1992 | Derby | |
| 5,358,476 A * | 10/1994 | Wilson | 604/74 |
| 5,385,251 A * | 1/1995 | Dunn | 215/11.3 |
| 6,050,432 A | 4/2000 | Koehnke | |
| 6,152,408 A | 11/2000 | O'Grady | |
| 6,196,717 B1 | 3/2001 | Belias et al. | |
| 6,257,847 B1 | 7/2001 | Silver et al. | |
| 6,481,594 B1 | 11/2002 | Yeh et al. | |
| 6,547,756 B1 | 4/2003 | Greter et al. | |
| 6,575,202 B2 * | 6/2003 | Lafond | 141/10 |
| 6,576,278 B1 | 6/2003 | Sprehe | |
| 6,899,239 B1 * | 5/2005 | Gray | 215/11.3 |
| 6,938,836 B2 * | 9/2005 | Bouic | 239/346 |

(Continued)

FOREIGN PATENT DOCUMENTS

| GB | 2450996 | 1/2009 |
|---|---|---|
| WO | 02/081003 | 10/2002 |

OTHER PUBLICATIONS

GTZIP. "GTZIP.com—Hang Hole 2 Mil. Bags." <http://www.gtzip.com/ziplock/hanghole2mil.html> (Jul. 4, 2004).*
International Search Report and Written Opinion for International Patent App. No. PCT/US2011/044104, completed Nov. 8, 2011.

*Primary Examiner* — Nicholas Lucchesi
*Assistant Examiner* — Melissa A Snyder
(74) *Attorney, Agent, or Firm* — McDonnell Boehnen Hulbert & Berghoff LLP

(57) ABSTRACT

An attachment arrangement is disclosed for attaching a milk collecting bag to a breastpump assembly. In one form this includes an adaptor having mounting ears upon which portions of a bag with apertures therein are hung to suspend the bag in place below the breastpump assembly.

19 Claims, 3 Drawing Sheets

U.S. PATENT DOCUMENTS

| | | | |
|---|---|---|---|
| 6,962,439 B2 * | 11/2005 | Taheri | 383/61.2 |
| 7,048,441 B2 | 5/2006 | Pape | |
| 7,727,182 B2 | 6/2010 | Silver | |
| 2002/0156419 A1 * | 10/2002 | Silver et al. | 604/74 |
| 2006/0074379 A1 | 4/2006 | Hunt | |
| 2010/0072160 A1 * | 3/2010 | Hayes | 215/11.1 |

* cited by examiner

BAG ATTACHMENT DEVICE FOR BREASTPUMP

FIELD OF THE INVENTION

This invention relates to a device for releasably attaching a milk receiving bag to a breastpump, and to the bag that is connected to the breastpump by the device.

BACKGROUND OF THE INVENTION

Breastmilk pumps are well known and are generally comprised of a hood or shield that fits over a portion or the entire breast, a vacuum pump connected to the hood for generating an intermittent pressure variation within the hood, and a receptacle or container for the expressed milk. The receptacle in such an arrangement is often a rigid plastic feeding bottle well known to those in the art. It is also known to use a plastic bag as the receptacle, sometimes in combination with a rigid outer shell supporting the bag. There are manually driven vacuum pumps (e.g., handheld piston pumps) which most commonly connect at or closely adjacent to the hood, as well as vacuum pumps that are driven by an electric motor and interconnect to the hood via tubing. The vacuum pumps of these devices intermittently generate a pressure, most typically a vacuum (or a negative pressure) within the hood, with the hood encompassing the nipple and a substantial amount of the breast. The intermittent suction action of the pump serves to pull on and/or compress the breast, drawing it within the narrowing funnel of the hood, to thereby express milk in an action reminiscent of suckling. The milk so extracted typically flows from the hood into a container, e.g., a bottle or a bag, for storage and later use. A breastpump of the foregoing type is shown in U.S. Pat. No. 4,857,051.

As noted, plastic bags have been proposed and adapted for use with a breastpump to function in the above-described manner. The method of using and storing these types of bags are well-documented as are the advantages. See for instance, U.S. patent Publication No. 2002/0156419. Where bags are used independently of a bottle, this eliminates the need to then transfer milk from a container (bottle) to a plastic bag for storage. The presence of the bag makes unnecessary the step of cleaning a container after use. Attaching the bag to the pump in a simple and straightforward manner for the mother is something worthy of achieving, however.

SUMMARY OF THE INVENTION

The present invention in one embodiment provides a breastpump having a breast shield with a first end for placement on a breast and a second end for connection to an attachment device. The attachment device in one form is an adaptor having at least one mounting ear (or hook), and uses a milk collection bag having an aperture that connects to the at least one mounting ear. The adaptor attaches to the standard breastpump assembly much the same as a bottle would, e.g., by matching screw threads. The adaptor serves to suspend the bag open at the top directly beneath the conduit structure of the breastpump assembly, through which milk flows, such that the milk flows into the open bag.

The attachment device in a preferred form is an adaptor connectable to the breastpump having mounting ears on opposite sides. In another embodiment, the ears are formed as part of a modified breastpump assembly. A bag having apertures adapted to connect to the mounting ears allows the bag to be easily attached and removed from the adaptor.

In yet another embodiment, a bag for collecting mother's milk is provided including front and back sides, each of the front and back sides having an aperture therein for use in hanging the bag from the attachment device.

In yet another embodiment, a method for attaching a milk bag to a breastpump is disclosed, the method including providing an adaptor having mounting ears, providing a bag having apertures adapted to engage over the mounting ears, first putting one mounting ear through a bag aperture, and then putting the other mounting ear through another bag aperture, and attaching the adaptor to the breastpump assembly (either before or after the bag is mounted), with the bag open beneath a conduit structure through which milk passes.

These and other features and advantages of the present invention will be further understood and appreciated when considered in relation to the following detailed description of embodiments of the invention, taken in conjunction with the drawings, in which:

DETAILED DESCRIPTION OF EMBODIMENTS OF THE INVENTION

Figure 1:
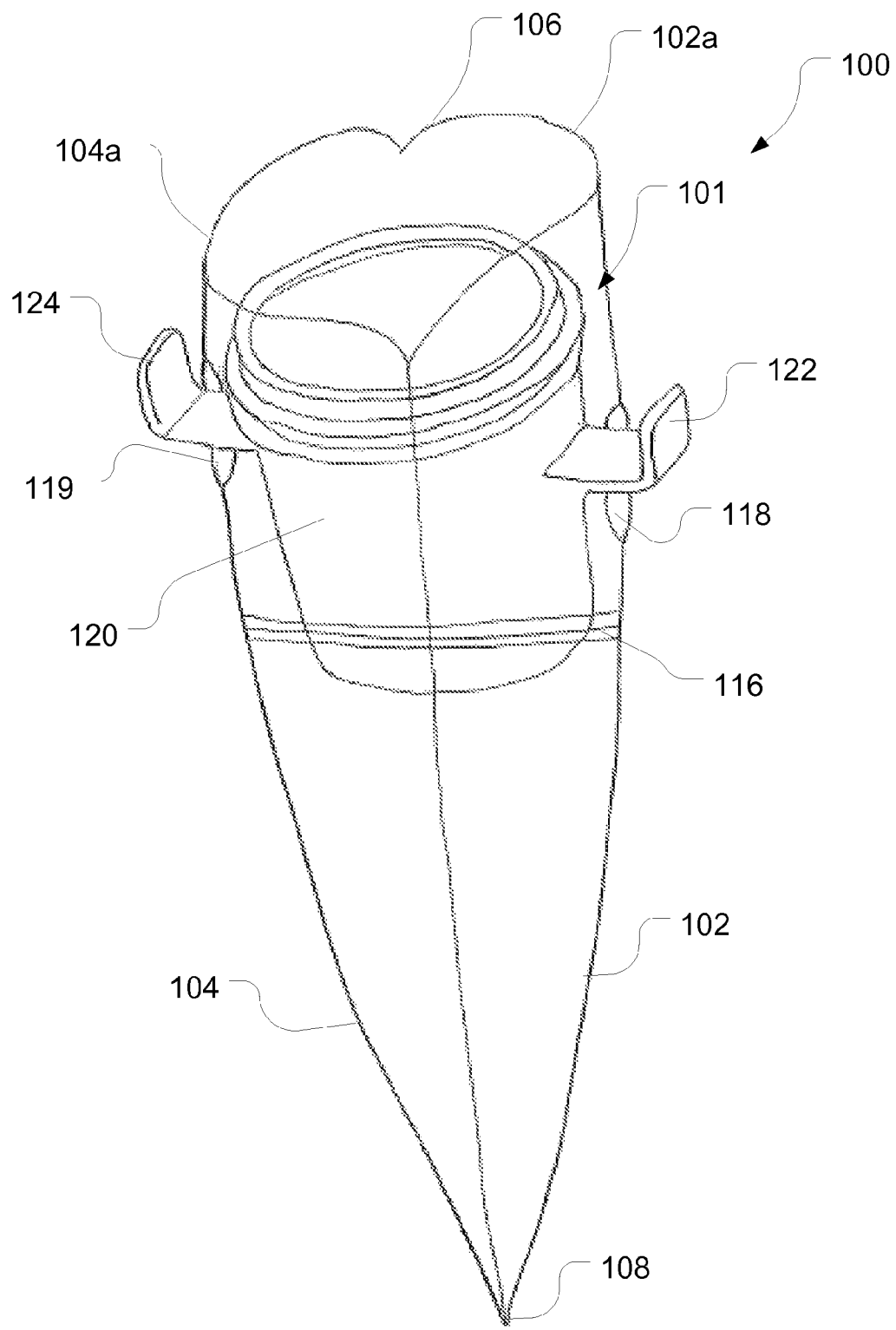
FIG. 1 is a perspective view of an embodiment of an attachment device and related bag according to certain aspects of the present invention.

One embodiment of the invention is shown in an attachment arrangement of FIG. 1. This type of attachment arrangement in the form of an adaptor and related bag is simply illustrative, and not intended to be limiting of the invention. Referring to FIG. 1, the attachment arrangement 100 includes a bag 101 and an adaptor or base member 120. The bag 101 receives and stores breastmilk pumped from a breastpump, such as breastpump assembly 200 (shown in FIG. 4). The bag 101 itself is, except for the special adaptation for attaching to the adaptor described hereafter, fairly standard. It could be made in many ways known in the art, such as here, being comprised of a front sheet 102 and a back sheet 104. The front and back sheets (sides) 102, 104 are made of a suitable liquid impervious food compatible plastic, such as polyethylene, as described in U.S. Pat. Pub. No. 2006/0074379, the contents of which are incorporated herein by reference.

Figure 5:
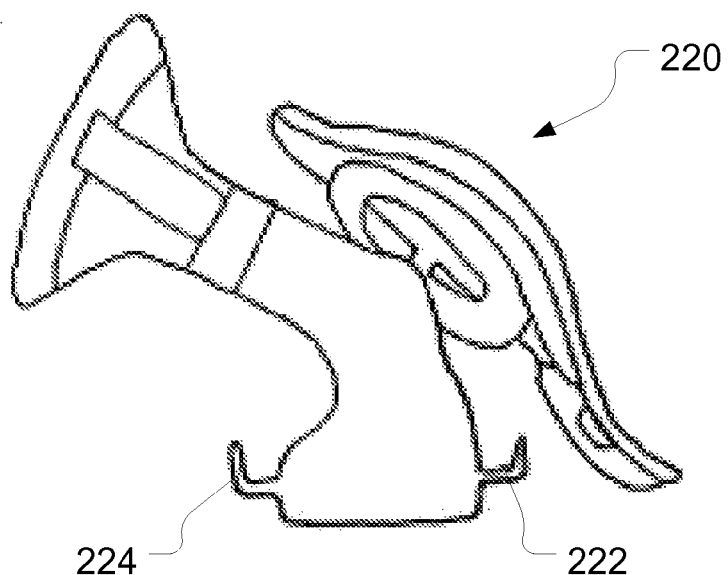
FIG. 5 is a side view of an alternate embodiment of the invention.

The breastpump assembly 200 may be a manual breastpump, such as the breastpump disclosed in U.S. Pat. No. 7,727,182, the contents of which are also incorporated herein by reference. Alternatively, the attachment arrangement 100 may be used with an electric breastpump, such as U.S. Pat. Nos. 6,547,756 or 6,257,847, each of can be referred to for details of the breastpumping equipment in general. In this embodiment, the breastpump assembly itself is not significant, in that the adaptor 120 is intended to attach to a standard-issue breastpump assembly, e.g., a breastpump assembly that is manufactured for a bottle to be attached thereto; FIG. 5, however, shows a modified breastpump assembly.

Figure 2:
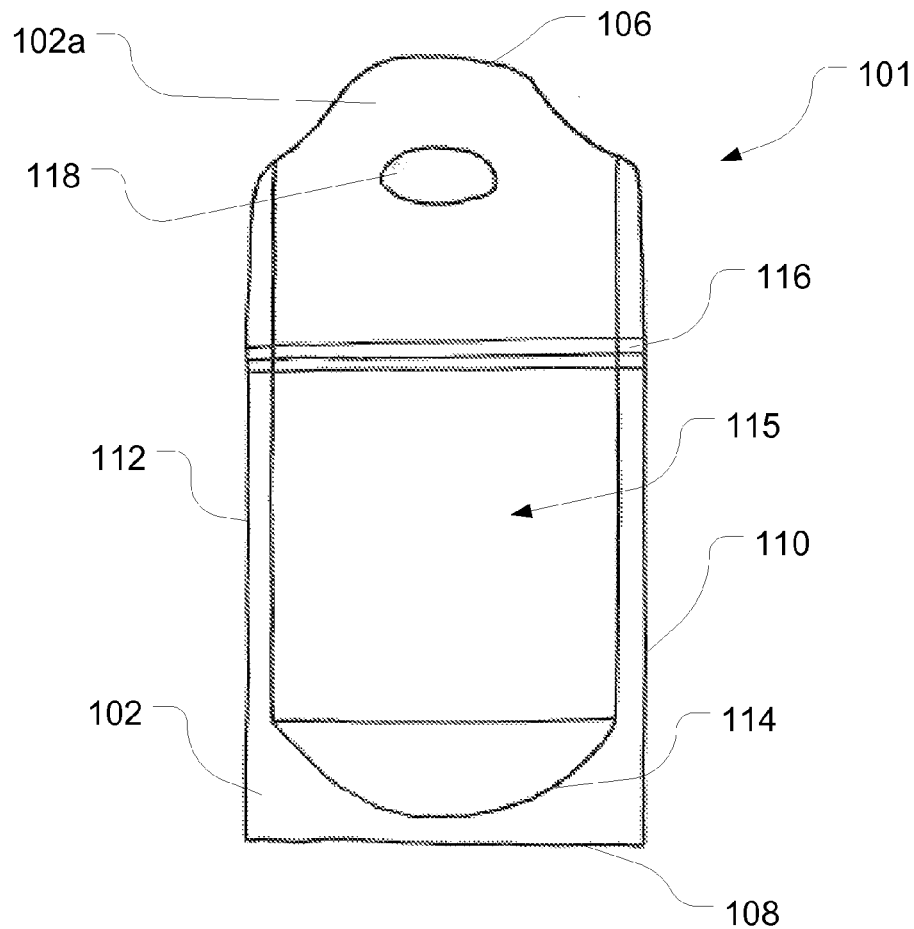
FIG. 2 is an elevational view of the milk storage container shown in FIG. 1.

Referring now to FIGS. 1 and 2, the bag 101 further includes a top edge 106, a bottom edge 108, and two side edges 110, 112. A gusset structure having seal 114 is formed near the bottom edge 108. The gusset structure is formed by conventional methods, e.g., by providing a folded panel of pouch material adjacent the bottom edge 108 of the bag 101 and sealing the material into a gusset structure. The gusset structure lends strength to the region and even the ability to stand the bag when filled.

A resealable or reclosable seal 116 is provided for access to the bag interior when in an open condition, and seals the bag when in a closed condition. In one embodiment, the reclosable seal 116 is preferably a "zip" type closure or an equivalent, formed by attaching to either front sheet 102 or back sheet 104, an extended male element above and essentially parallel to bottom edge 108, the male element being press fit into a corresponding female channel-type element attached to the other of the front and back sheet 102, 104. A number of known designs exist for "male/female" zip-type closures. Some are designed to fasten together to merely place a bag in a closed condition, and some are designed to retain fluids within the bag in a leak-proof fashion. Of course, other mechanisms of sealing the bag are contemplated for use in the present invention to seal the bag in a reclosable fashion. Reclosable seal 116 extends between side edges 110, 112 and is also located below top edge 106. Thereby, when reclosable seal 116 is closed, the combination of reclosable seal 116, sealed side edges 110, 112 and sealed pouch bottom edge 114 define a generally rectangular bag pouch 115 suitable for retaining fluids therewithin.

A portion of each of front sheet 102 and back sheet 104 extends beyond reclosable seal 116, respectively portions 102a and 104a. The bag 101 also includes apertures 118, 119 located on the front and back portions 102a and 104a, respectively. The apertures 118, 119 support the bag 101 on the adaptor 120, which is described in detail below. Although the apertures 118, 119 are shown having a generally oval shape, it should be understood that the apertures may take any suitable shape, including a simple slit.

Bag 101 may further include a label area (not shown) located on the outer side of front sheet 102, of sufficient dimensions to allow for some information to be provided on bag 101 regarding the contents in the bag, such as, for example, "DATE", "VOLUME" and "NAME", either by writing directly on front sheet 102, or indirectly by adhering an optional label at this location. Other locations for information may be provided. Calibrated markings (not shown) as for milk volume may additionally be provided.

Figure 3:
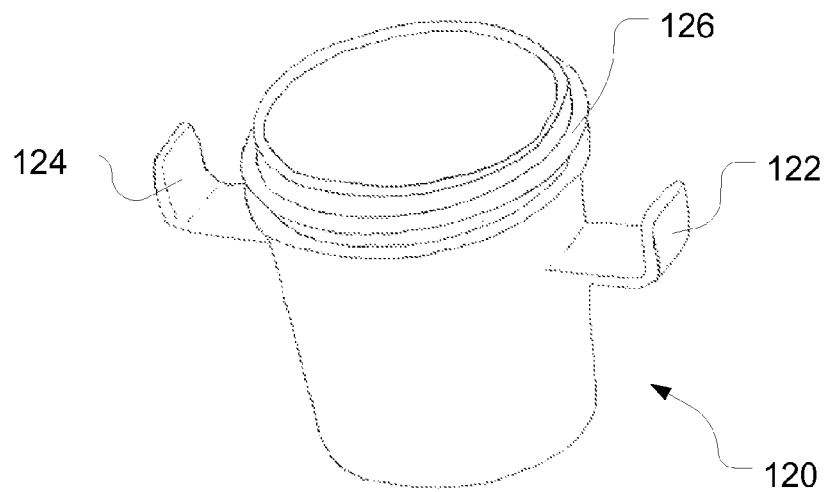
FIG. 3 is a perspective view of an adaptor shown in FIG. 1.
Figure 4:
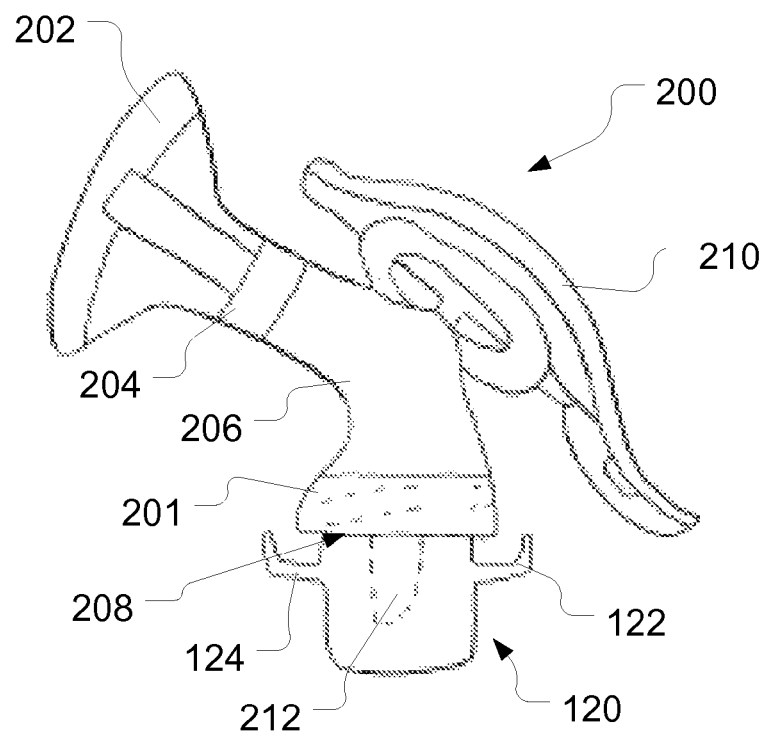
FIG. 4 is a side view of the adaptor shown in FIG. 1 attached to a breastpump assembly.

Referring to FIG. 3, the adaptor 120 connects the bag 101 to a breastpump assembly, such as breastpump assembly 200 shown in FIG. 4. The adaptor 120 may comprise a generally cylindrical or tubular shape, serving as a base member. Alternatively, the adaptor 120 may take any suitable shape. The base member of the adaptor 120 extends below the recloseable seal 116 of the bag 101 to help prevent overflow of the bag 101. The adaptor 120 includes at least one mounting element or ear 122 for insertion through aperture 118 of the bag 101, but preferably further includes a second mounting element or ear 124 for insertion through the second aperture 119 of the bag 101. It should be understood that the mounting elements 122, 124 may comprise ears, hooks, buttons, posts, protuberances, or any other suitable mounting element from which a bag may hang. The mounting elements maybe located on opposite sides or areas of the adaptor 120.

The adaptor 120 attaches to the breastpump by a connector portion 126. In one embodiment, the connector portion 126 may be a threaded mechanism, match-threaded to a collar 201 of a standard breastpump assembly. However, it should be understood that the connector portion may comprise any suitable mechanism to secure the adaptor 120 to the breastpump assembly, as long as the connector portion 126 and collar 201 have cooperating connection mechanisms. The cooperating portions releasably mechanically connect the adaptor 120 to the collar 201 in any suitable manner as long as a portion of the adaptor communicates with a milk outlet of the breastpump assembly.

Referring now to FIG. 4, a breastpump assembly 200 includes a funnel-shaped breast shield 202 that is sized and shaped for engagement with at least a portion of a breast. Downstream from the breast shield 202 is a cylindrical extension 204 which is connected (or connectable) to a receiving portion of a pump housing 206. Upstream and downstream are used relative to milk flow in use of the invention. The pump housing 206 includes a conduit structure (not shown) for conveying expressed breastmilk from the breast shield 202, through extension 204 and out through an outlet 208 of the internal conduit structure. In the given example, this is a lever pump (manual) mechanism 210 connected to the housing 206 to provide a cyclical negative pressure at the breast shield 202. Further details of this pump mechanism 210 and associated components, including the conduit structure and related valving, such as valve 212, as well as operation, can be gleaned from U.S. Pat. No. 7,727,182. Again, the specific breastpump is incidental to the inventive attachment arrangement in this embodiment using an adaptor 120.

In operation, the adaptor 120 is placed on the collar 201 of the breastpump assembly 200. A user first places one mounting ear through a bag aperture, then places the other mounting ear through the other bag aperture. The bag 101 is then securely attached to the breastpump assembly opened and suspended beneath the conduit structure and outlet 208 to collect milk during a pumping session.

Alternatively, the bag 101 could first be attached to the adaptor 120, and then the mounted bag is positioned on the breastpump assembly 200 by attaching the adaptor 120 thereto.

In another embodiment, shown in FIG. 5, mounting elements or ears 222, 224 may be located directly on a breastpump 220, such as by molding therewith. Thus, no adaptor is used. The mounting ears 222, 224 are formed on the breastpump assembly in the vicinity of where milk would normally exit from the breastpump assembly into a container at outlet 226. The outlet 226 extends below the recloseable seal 116 of the bag 101.

Thus, while the invention has been described herein with relation to certain embodiments and applications, those with skill in this art will recognize changes, modifications, alterations and the like which still come within the spirit of the inventive concept, and such are intended to be included within the scope of the invention as expressed in the following claims. For instance, while the bag has been described with a particular aperture, other ways to yield an opening in the upper part of the bag are known in the art, such as slits, an area of perforations which can then be breached, a thinned portion which can be punctured, and so on. In a similar vein, while the bag has been described as being hung from ears or hooks, other elements could fulfill the same function, such as buttons, pins, posts, and so forth.

Further, in an alternate embodiment, the adaptor 120 may comprise clips or pins, for example, which attach to a standard milk collection bag. In this embodiment, the milk collection bag would not have apertures or any corresponding mounting features.

What is claimed is:

1. An attachment arrangement for attaching a milk bag to a breastpump comprising:

an adaptor including a connector portion which mates with a part of a breastpump assembly that is manufactured for a bottle to be attached thereto using a bottle connection mechanism, the adaptor being used in place of the bottle, the adaptor having at least two mounting ears, the ears being between first and second end ends of the adaptor extending generally radially outward beyond the bottle connection mechanism;

a bag having an aperture formed adjacent one end adapted to connect to the at least two mounting ears with the bag thereby suspended beneath the breastpump assembly when the adaptor is mated.

2. The attachment arrangement of claim 1 wherein the adaptor connector portion is a threaded mechanism for connection to the breastpump assembly.

3. A method for attaching a milk storage bag to a breastpump assembly comprising:

providing an adaptor having mounting ears, the mounting ears extending generally radially outward beyond a connection mechanism for attaching a bottle to the breastpump assembly;

providing a bag having apertures adapted to engage over the mounting ears;

putting one mounting ear through a bag aperture, then putting the other mounting ear through another bag aperture, and either before or after mounting the bag thereto, attaching the adaptor in place of a bottle on the breastpump assembly.

4. An attachment for a breastpump assembly comprising:
An adaptor having mounting ears formed thereon,
said mounting ears being between first and second ends of said adaptor,
extending generally radially outward beyond where a container mouth would normally attach to the breastpump assembly, the adaptor adapted to be attached to a breastpump assembly in the vicinity of where milk would normally exit from the breastpump assembly into a container, the mounting ears adapted to engage with apertures in a milk bag to suspend the milk bag in place to receive milk.

5. A breastpump comprising:
a breast shield having a first end for placement on a breast;
a conduit structure communicating with the breast shield which conveys expressed milk to an outlet;
a collar providing a connection mechanism for a container to receive breastmilk from the outlet;
an attachment device for attaching a milk collection bag in place beneath the outlet, the attachment device having at least two mounting elements extending generally radially outward beyond the connection mechanism and adapted to be received in an aperture of a milk bag in a manner so as to mount the milk bag beneath the outlet to receive expressed milk; and
a milk collection bag having an aperture provided therein through which the mounting element can extend to mount the milk collection bag in place.

6. The breastpump of claim 5 wherein the collar surrounds the outlet, and the attachment device is an adapter piece separate from the conduit structure, the adapter piece and the collar having cooperating portions to mechanically releaseably connect the attachment piece to the collar.

7. The breastpump of claim 6 wherein the adapter piece has mounting elements located on opposite sides thereof.

8. The breastpump of claim 7 wherein the mounting elements are ears.

9. The breastpump of claim 7 wherein the mounting elements are hooks.

10. The breastpump of claim 7 wherein the mounting elements are protuberances extending outwardly from the adapter piece.

11. The breastpump of claim 10 wherein the adapter piece has a generally cylindrical part which extends into the milk collection bag and serves to direct milk therein.

12. The breastpump of claim 11 wherein the milk collection bag includes a recloseable seal, and the generally cylindrical part extends below the recloseable seal.

13. The breastpump of claim 5 wherein the collar includes a threaded part and the adapter piece has matched threads to the collar.

14. The breastpump of claim 5 wherein the attachment device is a tubular-shaped element, and the mounting element is a protuberance extending outwardly from the tubular-shaped element.

15. The breastpump of claim 14 wherein the collar surrounds the milk outlet, the collar including a threaded part, and the tubular-shaped element having matched threads to the collar.

16. The breastpump of claim 15 wherein the attachment device has mounting elements located on opposite sides thereof.

17. The breastpump of claim 16 wherein the mounting elements are ears.

18. The breastpump of claim 16 wherein the mounting elements are hooks.

19. An attachment arrangement for attaching a milk bag to a breastpump comprising:
a breast shield;
a conduit structure for conveying breastmilk from the breast shield to a collection container, the collection container attaching to the conduit structure with a connector mechanism;
an adaptor including a connector portion which mates with the connector mechanism, in place of the collection container, the adaptor having a pair of opposed hooks extending outwardly therefrom and beyond the connector mechanism; and
a bag that is configured to attach to the adaptor using a pair of opposed apertures in the bag to suspend the bag beneath the breastpump assembly when the adaptor is mated.

* * * * *